(12) United States Patent
Thiebaut

(10) Patent No.: US 6,642,413 B2
(45) Date of Patent: Nov. 4, 2003

(54) PROCESS FOR MONITORING A CONTINUOUS ACETIC ACID AND/OR METHYL ACETATE PRODUCTION

(75) Inventor: Daniel Thiebaut, Lescar (FR)

(73) Assignee: Acetex Chimie, Neuilly sur Seine Cedex (FR)

( * ) Notice: Subject to any disclaimer, the term of this patent is extended or adjusted under 35 U.S.C. 154(b) by 8 days.

(21) Appl. No.: 09/950,819

(22) Filed: Sep. 13, 2001

(65) Prior Publication Data

US 2003/0018213 A1 Jan. 23, 2003

(30) Foreign Application Priority Data

Jul. 3, 2001 (FR) .............................. 01 08798

(51) Int. Cl.[7] .......................... C07C 51/10; C07C 51/12; C07C 53/08; C07C 69/76; G05D 9/00
(52) U.S. Cl. ...................... 562/517; 562/519; 562/607; 560/232; 422/106; 422/110; 422/234
(58) Field of Search ................... 562/517, 519, 562/607; 560/232; 422/106, 110, 234

(56) References Cited

U.S. PATENT DOCUMENTS 5,352,415 A 10/1994 Ochiai

FOREIGN PATENT DOCUMENTS

EP 161874 5/1985
GB 1 002 785 A1 * 5/2000

* cited by examiner

*Primary Examiner*—Sreeni Padmanabhan
*Assistant Examiner*—Farhad Forohar
(74) *Attorney, Agent, or Firm*—Dennison, Schultz & Dougherty

(57) ABSTRACT

A continuous preparative process, including monitoring production, for acetic acid, methyl acetate or a mixture thereof, by carbonylation, in an industrial installation, of methanol or a carbonylatable derivative of methanol with carbon monoxide in a liquid phase in the presence of water and a homogeneous catalyst system. In a reaction zone I, the carbonylation is carried out in the liquid phase at a temperature of 150 to 250° C., under a pressure of $5 \cdot 10^5$ to $200 \cdot 10^5$ Pa and with venting of part of a gaseous canopy above a liquid phase level in said reactor. Then, in a vaporization or flash zone II, a liquid originating from the zone I at a pressure below that of zone I is partially vaporized to form a liquid fraction which is recycled into the reactor, and in a purification zone III, a vaporized fraction originating from flash zone II is distilled on a distillation column. At an outlet of the column, the product is recovered, other constituents of the vaporized fraction being at least partially recycled into said reactor. In the process, the reactor temperature and feed rate of the methanol or carbonylatable derivative in said reactor are brought under control of the carbon monoxide feed rate and of at least one of the parameters defining the composition of the reaction medium, or of the venting or of both the reaction medium and of the venting.

34 Claims, 2 Drawing Sheets

PROCESS FOR MONITORING A CONTINUOUS ACETIC ACID AND/OR METHYL ACETATE PRODUCTION

BACKGROUND OF THE INVENTION

The invention relates to a process for monitoring a continuous acetic acid and/or methyl acetate production.

More precisely, the invention relates to a method of improving the monitoring and control of a process for the preparation of acetic acid and/or methyl acetate.

Of the acetic acid manufacturing processes in common use, one of the most widely used in industry is the carbonylation of methanol or, more generally, a carbonylatable derivative of methanol with carbon monoxide. This reaction is carried out in the liquid phase under carbon monoxide pressure, carbon monoxide being one of the reactants, in the presence of a homogeneous catalyst system.

The rhodium-based carbonylation process is a known process which is exploited in industry and has formed the subject of numerous articles and patents, e.g. U.S. Pat. Nos. 3,769,329 and 3,813,428.

European patents EP 618 183 and EP 618 184, and European patents EP 785 919 and EP 759 022, describe a process for the carbonylation of methanol in the presence of an iridium-based catalyst system which may also contain rhodium.

A carbonylation process based on iridium and ruthenium, currently exploited in industry, is described in European patent EP 643 034.

The aim of improving these methanol carbonylation processes was to increase the productivity of the catalysts and reduce the acetic acid manufacturing costs.

The so-called "low water content" processes actually permit a considerable increase in acetic acid production, thereby limiting the level of investment required and lowering the operating costs by reducing the energy required to separate the acetic acid from the various constituents of the reaction mixture, particularly water.

Conventionally these different processes for the carbonylation of methanol in the liquid phase and in the presence of a homogeneous catalyst system are carried out in installations comprising three separate zones, as described in the article by M. J. HOWARD et al., Catalysis Today, 18 (1993) 325–354.

The reaction zone consists of a stirred continuous reactor operating under pressure (5–200 bar) and at elevated temperature (150–250° C.).

The methanol feed and a number of recycle streams are introduced at the bottom of the reactor. The carbon monoxide is dispersed in the reactor.

The liquid reaction medium produced is then sent to the second zone, called the vaporization zone or flash zone, in which the liquid is partially vaporized at a pressure below the reaction pressure.

This creates a flash, or adiabatic expansion, in which the majority of the light constituents (methyl iodide, methyl acetate and water) are vaporized together with the acid produced.

The flash zone makes it possible to separate the gas from the liquid; the vaporized stream then passes into the third zone, called the separation zone, while the liquid stream (essentially acetic acid containing the catalyst) is recycled into the first zone.

The purification zone can comprise one or more distillation columns; it makes it possible to separate the acetic acid and/or methyl acetate from the other constituents and to recycle the streams into the reaction zone.

In addition, a gas bleed at the top of the reactor makes it possible to monitor the level of carbon monoxide partial pressure and to remove the gaseous reaction by-products together with the inert gases present in the carbon monoxide feed.

The result of optimizing the current processes for the preparation of acetic acid is to maximize the acetic acid production in already existing equipment. To do this, the reaction is carried out with the concentrations of the various constituents of the reaction medium being kept at predetermined values so as to take advantage of the most appropriate kinetic conditions.

It then becomes essential to monitor the reactor and the recycle streams.

A variety of recent articles and patents have started to tackle this area.

The paper delivered by D. Z. TOBIAS at the IEEE Conference on Advanced Process Control, VANCOUVER, Apr. 29–30 1999, entitled "Adaptive Process Control of an Acetic Acid Reactor", shows the use of an external exchanger for making the material balance independent of the calorific balance, since without this exchanger it is impossible to vary the reactor output rate in order to maintain the reactor temperature, i.e. the reactor output rate is in effect dictated by the material balance.

The desired objective is to stabilize the reactor temperature in order to increase the production of the unit; the installation of a new monitoring system thus made it possible to reduce the standard deviation of the temperature from 3.6 to 0.8° C.

In continuous operations, it is customary to supply the carbon monoxide on demand under the control of the total pressure in the reactor.

The object of European patent application EP 0 983 752 is to install a monitoring system which aims to keep the carbon monoxide flow rate below a calculated maximum value representing an acceptable maximum flow rate.

The aim of European patent application EP 0 999 198 is to maintain the composition of the reaction medium, particularly the water and methyl acetate concentrations, in the carbonylation reactor by recycling a rich acetic acid stream coming from the acid purification zone.

Patents EP 0 846 674 and FR 2 750 984 describe the optimization of the CO consumption by introducing a second carbonylation reactor (finishing effect) between the 1st reactor (reaction zone) and the flash zone (vaporization zone).

U.S. Pat. Nos. 5,352,415 and 5,374,774 describe acetic acid manufacturing processes in which the levels of the reactor and the flash zone and the water concentration in the reaction medium are monitored.

U.S. Pat. No. 5,831,120 provides a technical solution for avoiding the accumulation of water in the reaction medium to give a target water concentration in the carbonylation reactor.

These various documents teach that, in the conventional process developed by MONSANTO, the heat of reaction was extracted via expansion of the reactor output, or flash, between the reactor and the flash zone. Thus, to monitor the reactor temperature, there was a fixed relationship between the flow rate of methanol entering the reactor and the flash rate. This led to a small variability in the level of liquid in the reactor and the intermediate process streams.

With the introduction of low water content processes, this system becomes inappropriate because the flash vaporization rate increases considerably due to the fact that the quantities of water evaporated are smaller and that they have to be replaced with much larger quantities of organic products whose latent heat of vaporization is lower than that of water.

This led to the installation of cooling exchangers for absorbing part of the heat of reaction, but this in turn increased the variability of the liquid levels in the reactor and the flash zone, as well as the liquid flow rates.

This great variation in liquid flow rates, in particular, leads to deficiencies in the process because it may be necessary to decrease production in order to reduce the stream entering the purification zone.

Furthermore, these fluctuations cause variations in the water concentration in the reactor and, as the reaction kinetics depend on the water concentration in the case of low water content processes, this again increases the risks of instability of the system.

The aim of patent application EP 1 002 785 is to maintain the methyl acetate concentration in the reactor at a predetermined value by adjusting the ratio of methanol to carbon monoxide, which regulates the feed rate of methanol in the reactor.

International patent application WO 00/37405 provides a method of monitoring the process by measuring the concentrations of the various components of the reaction solution by means of an infrared analyzer and, in response thereto, adjusting the concentrations of at least the catalyst species, the methyl iodide, the methyl acetate and the water in order to optimize the acetic acid production.

Whatever the case may be, the problem of monitoring the acetic acid reactor and maintaining particularly the water and methyl acetate concentrations has been clearly defined, but a means of achieving these objectives automatically has never been suggested.

Furthermore, no document has concerned itself with the problems presented by the larger or smaller fluctuations in the carbon monoxide stream entering the reactor, or sought to overcome the disadvantages which may result there from in terms of the acetic acid production.

SUMMARY OF THE INVENTION

The object of the present invention is precisely to overcome these disadvantages by providing a monitoring method which acts automatically to maintain particularly the water and/or methyl acetate concentrations and which makes it possible to maximize the acetic acid production when the CO feed rate undergoes fluctuations, as will be described below.

DETAILED DESCRIPTION OF THE INVENTION

It is pointed out first of all that:

The main methanol carbonylation reaction has the following equation:

$$CO+CH_3OH \rightarrow CH_3COOH$$

The main secondary reactions are:
The water gas reaction, also called WGSR (Water Gas Shift Reaction):

$$CO+H_2O \rightarrow CO_2+H_2$$

This reaction causes a loss of carbon monoxide with the simultaneous production of hydrogen and carbon dioxide.

It is important to evaluate this secondary reaction quantitatively relative to the main reaction. To use a criterion independent of the production level, one talks of hydrogen or $CO_2$ selectivity, the selectivity being expressed as the ratio of the number of moles of carbon monoxide taking part in the secondary reaction to the total number of moles of carbon monoxide taking part in the main reaction and the secondary reactions.

The propionic acid formation reaction with the following overall equation:

$$CH_3COOH+2H_2+CO \rightarrow H_2O+CH_3CH_2COOH$$

Hydrogen and carbon monoxide are thus consumed.

It may be pointed out here that part of the hydrogen generated by the above water gas reaction is consumed by the reaction to give propionic acid by-product. Thus, when the gas stream at the reactor outlet is analyzed, the hydrogen selectivity and $CO_2$ selectivity are no longer equivalent.

The $CO_2$ selectivity is more representative of the water gas reaction, but, for practical reasons associated with the gas analysis, it is not excluded to use the hydrogen selectivity for controlling the industrial installation.

The acetic acid and methanol esterification reaction to give methyl acetate The methyl acetate formed in this reaction can interfere with the separation of the liquid stream condensed at the top of the first purification column if its concentration increases without control in the reactor.

Depending on the carbon monoxide production process upstream of the acetic acid reactor, the carbon monoxide stream may not be totally constant. Small variations can be damped by installing a carbon monoxide buffer reservoir upstream of the acetic acid reactor, making it possible to reduce the variations in carbon monoxide flow rate and smooth them out over time insofar as the pressure level of the carbon monoxide source is greater than the pressure level at which it is consumed in the carbonylation reactor.

The result of larger fluctuations is that a carbon monoxide stream which can be defined as excess CO cannot be used in the reaction and then has to be discharged into the atmosphere, either via a flare stack or via a combustion system with heat recovery.

The invention consists in varying the reactor temperature and the methanol feed rate in the reactor for the purpose of adjusting the acetic acid production to the quantity of carbon monoxide available, while at the same time maintaining a low hydrogen or $CO_2$ selectivity or conditions which make it possible to optimize the CO consumption, especially by means of a preprogrammed electronic device such as a multivariable controller with predictive control.

Thus, in contrast to the previous modes of operation, where the reactor temperature remained fixed at a given value for long periods, the reactor temperature in the process according to the invention varies so that all the available carbon monoxide can be used.

It became apparent that, even though the parameters used as input variables in the controller were not the same, according to whether the process was one which is operated conventionally with a water content greater than or equal to 14% in the reaction medium, or whether it was a so-called "low water content" process, it was possible in all cases to optimize the acetic acid and/or methyl acetate production by means of a controller acting on the reactor temperature and the methanol feed rate (output variables or action variables)

as a function of the carbon monoxide feed rate and at least one additional parameter chosen as a set variable (input values or objective values).

Thus, according to its essential characteristic, the invention relates to a process for monitoring acetic acid and/or methyl acetate production in a continuous preparative process by the carbonylation of methanol or a carbonylatable derivative of methanol with carbon monoxide in the liquid phase, in the presence of water and a homogeneous catalyst system, said preparative process being carried out in an industrial installation comprising:

a zone I, called a reaction zone, comprising a reactor in which said methanol carbonylation reaction is carried out in the liquid phase at a temperature of 150 to 250° C., under a pressure of $5 \cdot 10^5$ to $200 \cdot 10^5$ Pa and with the venting of part of the gaseous canopy above the liquid level of the reaction medium in said reactor;

a zone II, called a vaporization zone or flash zone, in which the liquid originating from the reaction medium in zone I is partially vaporized at a pressure below that of zone I, the liquid fraction originating from this partial vaporization being recycled into the reactor; and a zone III, called a purification zone, in which the vaporized fraction originating from said flash zone II is distilled on one or more distillation columns, at the outlet of which the acetic acid and/or methyl acetate are recovered, the other constituents of said vaporized fraction being at least partially recycled into said reactor, wherein the reactor temperature and the feed rate of the methanol or carbonylatable derivative in said reactor are brought under the control of the carbon monoxide feed rate and at least one parameter defining the composition of the reaction medium and/or the vents.

The present invention therefore provides a better means of monitoring acetic acid and/or methyl acetate production in a continuous process for the carbonylation of methanol or a carbonylatable derivative of methanol with carbon monoxide in the liquid phase, in the presence of water and a homogeneous catalyst system, said process being carried out in an industrial installation comprising three main zones I, II and III defined above.

"Carbonylatable derivative of methanol" is understood as meaning any of the methanol derivatives conventionally used in industrial processes for the preparation of acetic acid and/or methyl acetate by carbonylation, for example dimethyl ether, methyl halides or methyl acetate.

The monitoring process according to the invention can be carried out by means of any electronic device for assuring the desired servo-control so as to minimize the carbon monoxide losses when the carbon monoxide feed undergoes fluctuations.

In particular, this servo-control device can be an electronic control device preprogrammed for this purpose.

More precisely, the servo-control device acts on the reactor temperature and on the methanol feed rate in the reaction so as to minimize the carbon monoxide losses by continuously monitoring the carbon monoxide feed rate in the reactor and at least one of the parameters defining the composition of the reaction medium and/or the vents.

Those skilled in the art will easily understand that the parameter chosen as the input for the device for effecting the servo-control depends on the mode of operation of the acetic acid and/or methyl acetate manufacturing process, and that, in particular, these parameters may be different according to whether the process is a so-called conventional process of the Monsanto type or a so-called "low water content" process, as will be apparent from the following description.

The control device can be either a monitoring-control system if it possesses the requisite functions, or a multivariable predictive controller, or any other electronic system having the following characteristics:

an input/output (I/O) device;
an interface for digital conversion of the analog inputs/outputs; and
a calculating processor.

However, a multivariable predictive controller was chosen for the examples, on the one hand to escape the specific characteristics associated with monitoring-control systems, and on the other hand to be able to make direct use of the programs supplied with the multivariable controller.

Such a device is based on the use of a mathematical control model and enables a predictive control which, by relying on this mathematical model, produces a hypothesis about the future of the variable to be monitored.

The commercially available multivariable predictive controllers generally incorporate a library of mathematical control models.

Before it can be used, a multivariable predictive controller has to be programmed, which is generally carried out in the following manner:

A mathematical model is chosen from the above-mentioned library as a function of the reactor used and the chemical reaction which it is desired to perform. This choice is typically made empirically by means of preliminary tests which consist in testing all the mathematical models on the chemical reaction in question and observing the control responses obtained.

Values of so-called action variables and corresponding values of so-called objective variables are then supplied to the controller. The action variables are the variables which are to be acted upon so that the objective variables are regulated around desired set values. In the present invention the action variables consist of the reactor temperature and the methanol flow rate and the objective variables consist of the carbon monoxide feed rate and the above-mentioned parameter defining the composition of the reaction medium and/or the vents.

This second phase amounts to the creation, in the controller, of a database representing the relationships between the action variables and the objective variables.

A calculating program, supplied with the controller, then optimizes the control parameters, such as the gain and the lag, which will have to be applied to the controller's electrical output signals in order to control devices (typically valves) acting on the action variables.

The values of the action variables and objective variables which are supplied to the controller are obtained during a preliminary experimental phase, without control, which consists in carrying out the chemical reaction, rapidly increasing the value of one of the variables by increments so as to cause the system to change, and observing the change in the different variables by measuring their value continuously.

Once the controller has been programmed, it is integrated into the control station and progressively looped into the process.

When the process is carried out, the controller regulates the objective variables around set values by acting on the action variables via the above-mentioned devices.

In a first variant, the invention applies to the monitoring of conventional processes for the carbonylation of methanol to acetic acid and/or methyl acetate with water contents greater than or equal to 14%.

It is well known that, in such a conventional process for the carbonylation of methanol to acetic acid and/or methyl acetate in the liquid phase, catalyzed by rhodium, with water contents greater than or equal to 14%, the carbon monoxide is introduced under the control of the total pressure in the reactor; the methanol is introduced at a fixed rate to give the desired acetic acid production at a fixed reactor temperature.

This monitoring method works if the catalyst is sufficiently active.

If this is not the case, the methanol not converted to acetic acid esterifies to methyl acetate. The increase in methyl acetate concentration in the reactor causes poor performance in the purification zone, particularly at the top of the first purification column, where the increase in methyl acetate concentration first impairs and then inhibits the separation of the condensed liquid into two different liquid phases (a light aqueous phase, part of which serves as column reflux and part of which is recycled into the reactor, and a heavy organic phase, all of which is recycled into the carbonylation reactor).

The production level then has to be reduced in order to correct the situation, after which more catalyst is added or the reactor temperature is increased in order to allow operation at a higher production level.

It has been found that the reaction can be better controlled by monitoring the secondary water gas reaction which produces hydrogen and carbon dioxide.

Continuous or sequential analysis of the plant's purge gases, coupled with measurement of the total flow rate of the plant's vents, makes it possible to determine the hydrogen and carbon dioxide flow rates generated by the secondary reactions in the carbonylation reactor.

The ratio of these partial flow rates to the total flow rate of carbon onoxide entering the reactor provides access to the selectivities.

It may be pointed out here that part of the hydrogen generated by the water gas reaction, WGSR, is consumed by the reaction to give propionic acid by-product, so the hydrogen selectivity and $CO_2$ selectivity are no longer equivalent.

The $CO_2$ selectivity is more representative of the water gas reaction, but on certain occasions, for practical reasons associated with the gas analysis, the hydrogen selectivity may be used to control the industrial installation.

Thus, in the first variant of the invention, the reaction is monitored well by varying the flow rate of methanol, or carbonylatable derivative of methanol used, at the reactor inlet, and the reactor temperature, to give a hydrogen or $CO_2$ selectivity less than or equal to 0.01 and/or a methyl acetate concentration in the reactor of less than 5% by weight, preferably of less than 2% by weight, making it possible to assure a good decantation at the top of the first purification column.

The tests performed by the inventor of the present invention have clearly demonstrated that by acting via the controller on the reactor temperature and the CO feed rate, it is possible to limit the CO losses when the carbon monoxide feed rate in the reactor varies, by imposing a set value less than or equal to 0.01 on the $CO_2$ or $H_2$ selectivity and/or by maintaining the methyl acetate concentration at a value of less than 5% by weight, preferably of less than 2%, in the reaction medium.

Thus, in this first variant, where the water concentration in the reaction medium is greater than or equal to 14% by weight, the control involves the $CO_2$ or $H_2$ selectivity and the flow rate of CO to be consumed, and the controller acts both on the reactor temperature and on the flow rate of methanol (or carbonylatable derivative) entering the reactor.

Using the control device in this first variant of the invention made it possible to maintain the $CO_2$ (or hydrogen) selectivity within narrow limits of variation by acting on the reactor temperature and on the feed rate of methanol (or carbonylatable derivative) in the reactor, and made it possible to optimize the carbon monoxide consumption, even in the presence of relatively large fluctuations in the carbon monoxide feed rate in the reactor.

In a second variant, the invention is also applicable to so-called "low water content" processes for the manufacture of acetic acid and/or methyl acetate in the liquid phase, in the presence of a homogeneous catalyst, i.e. to the case where the water concentration in the reaction medium is less than 14% by weight.

It is well known that, in contrast to the conventional processes where the water concentration is greater than or equal to 14% by weight of the reaction medium, the water concentration in such "low water content" processes is a direct parameter of the kinetics of the acetic acid production reaction, whereas the carbonylation reaction is relatively insensitive to the $CO_2$ selectivity; for this reason, those skilled in the art will easily understand that, in such a case, contrary to the previous case, the water concentration in the reaction medium, rather than the $CO_2$ selectivity, will be chosen as a parameter used as an objective variable of the controller.

Therefore, the water concentration, which will be fixed at a predetermined value, and the flow rate of carbon monoxide entering the reactor will advantageously be chosen as objective variables of the controller for the "low water content" manufacturing processes.

It became apparent that, in this case too, it was possible to act via a preprogrammed controller, particularly via a multivariable predictive controller, on the reactor temperature and the flow rate of methanol entering the reactor in order to maintain the water concentration at said predetermined value and to optimize the consumption of carbon monoxide when its feed underwent fluctuations.

In one advantageous variant applicable to both the embodiments of the invention described above, it seemed particularly useful also to bring the flow rate of liquid passing from reaction zone I into flash zone II, and the flow rates of recycle liquid passing from zones II and III into the reactor, under the control of the liquid level in the reactor so that the level remains fixed at a predetermined value.

This predetermined value is advantageously fixed at between 50 and 100% of the absolute total scale of the levels in the reactor.

Thus the controller used according to the invention can also be used to regulate the liquid level in the reactor by adding to the controller, as an action variable, the flow rate of liquid from the reactor into the flash zone and the various return flow rates into the reactor, particularly the liquid flow rates and streams originating from zones II and III.

In another particularly advantageous variant of the invention, the servo-control device used according to the invention, particularly the multivariable predictive controller, can be used to monitor and regulate the water content in the reaction medium.

In particular, it can be used to monitor and regulate on the one hand the equipment for avoiding the accumulation of water in the reaction medium, particularly in the case of a distillation column for extracting water from the process for the preparation of acetic acid.

With the same objective of monitoring the water content of the reaction medium, said device can also be used to monitor and regulate said flow rate or flow rates of methyl acetate, dimethyl ether or acetic anhydride introduced to replace part of the methanol feed, for the purpose of adjusting the water content in the reactor.

In another particularly advantageous variant of the invention, in order to relieve the purification train, it is possible to add exchangers for absorbing part of the heat of the acetic acid production reaction. Monitoring of the reactor temperature is then based on monitoring of the heat exchanged in this way, and it has been possible to show that the system according to the invention does indeed enable all the available carbon monoxide to be used effectively with a good control of the composition in the reactor (methyl acetate).

In another variant of the invention, part of the heat of the acetic acid production reaction can be removed or recovered.

This removal or recovery can be effected either at the reactor outlet via a heat exchanger placed on a loop for recirculating reaction liquid into said reactor, or at the reactor inlet on recycle streams entering said reactor.

In another variant, the fluctuations or variations in the carbon monoxide feed rate can be damped via a buffer reservoir placed upstream of said reactor.

In this variant, a set value of the carbon monoxide flow rate is made to depend on the pressure inside said buffer reservoir.

In another variant of the invention, the fluctuations in the flow rate of carbon monoxide entering the reactor can be damped by discharging at least part of the excess into the atmosphere.

This discharge may be effected particularly in conventional manner, either via a flare stack or via a heat recovery system.

Finally, it became apparent that it was particularly advantageous to couple the control device used according to the invention with an analyzer, operating in the near infrared region, for measuring the concentrations of water and methyl acetate and/or methyl iodide in the reaction medium.

This coupling of a real-time process analyzer based on analysis in the near infrared region was found to be particularly valuable in the "low water content" processes, where it is important to control not only the methyl acetate concentration but also the water content, which has a direct influence on the kinetics of the acetic acid and/or methyl acetate production reaction.

In general, the monitoring process of the invention is applicable to any continuous processes for the manufacture of acetic acid and/or methyl acetate in the liquid phase, in the presence of a homogeneous catalyst system.

It is very particularly applicable to manufacturing processes in which the catalyst system comprises at least one group VIII metal, particularly rhodium, iridium or platinum.

It is also applicable, particularly advantageously, to carbonylation processes in which the catalyst system also comprises at least one co-catalyst, particularly

BRIEF DESCRIPTION OF DRAWINGS

The invention will become more clearly apparent from the following Examples described with reference to the attached Figures, in which.

EXAMPLES

Example 1

(Comparative)

Figure 1:
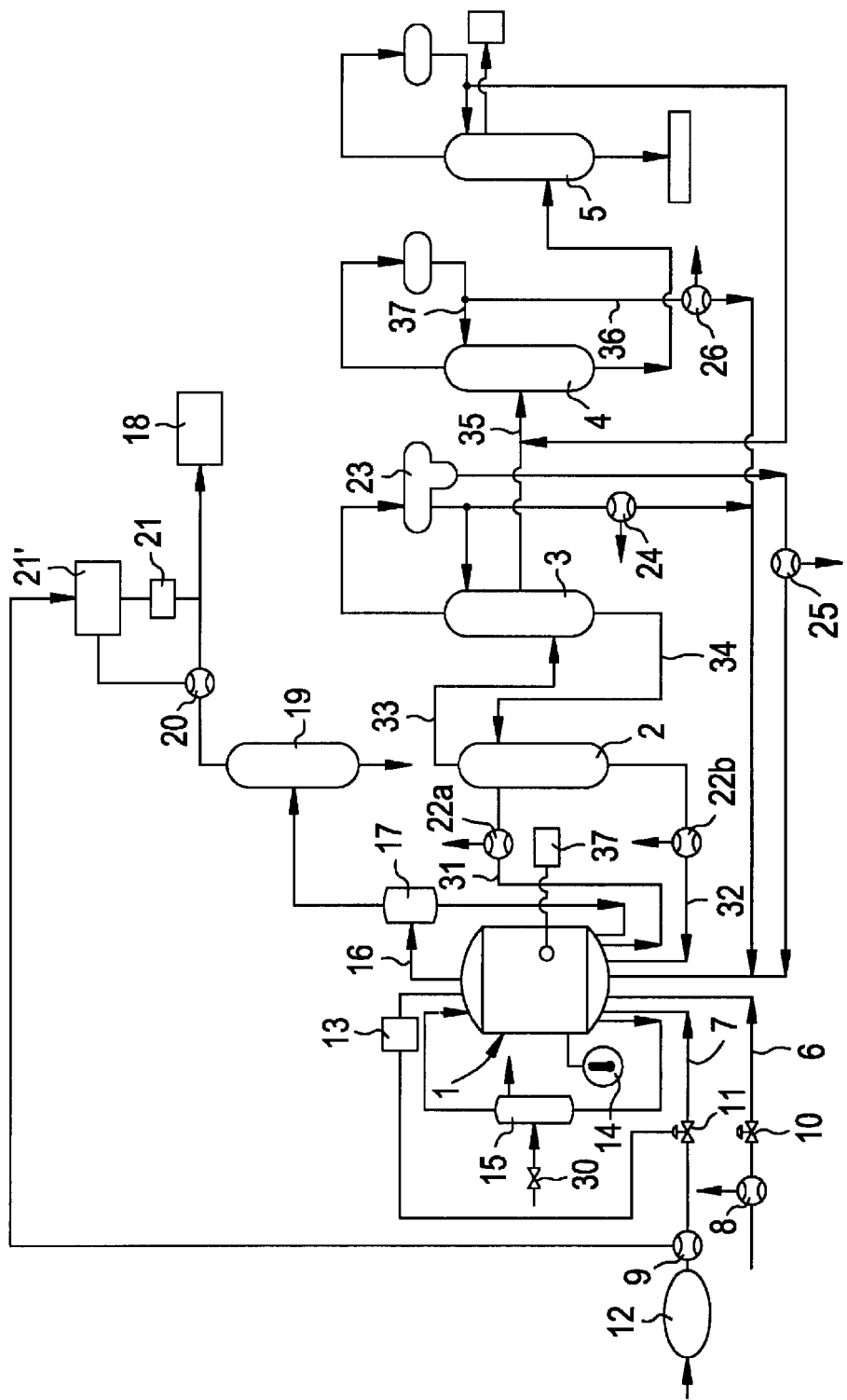
FIG. 1 shows the diagram of the installation according to the prior art for the manufacture of acetic acid by carbonylation. This Figure is given with reference to Example 1.

In this Example, acetic acid is prepared by the carbonylation of methanol with carbon monoxide in the liquid phase, in the presence of a homogeneous catalyst system, in an installation shown diagrammatically in FIG. 1.

The carbonylation reaction is carried out at a temperature of 185° C. under a total pressure of 29 bar absolute.

The water concentration is maintained at a value of 14% by weight of the reaction medium.

The concentrations are as follows, expressed by weight of the reaction medium:

Water: 14%
Methyl iodide: 10%
Methyl acetate: 1.75%
Acetic acid and catalysts: to 100%

The acetic acid production is 54.1 T/h.

The installation comprises a reaction zone I consisting essentially of a reactor 1, a flash zone II comprising essentially a flash device 2, and a purification zone III comprising three distillation columns 3, 4 and 5 in the case shown in this Figure.

The carbon monoxide is supplied after purification in a cryogenic separating system (not shown in the Figure) involving washing with liquid methane.

Its purity varies from 98 to 99% (these percentages being expressed by volume/volume), depending on the efficiency of the purification equipment.

The carbon monoxide is then introduced into the bottom of the reactor 1 via a line 7 equipped with a flow meter 9 and an inlet valve 11. A carbon monoxide buffer reservoir 12, located upstream of the inlet valve 11, makes it possible to dampen any variations in the CO feed rate in the reactor 1.

The methanol is also introduced into the bottom of the reactor 1 via a line 6 equipped with a flow meter 8 and an inlet valve 10.

The means of introducing the other components of the reaction medium, such as the water, the catalyst system and any solvents in particular, are not shown in the diagram of FIG. 1.

A pressure controller 13, connected to the carbon monoxide inlet valve 11, makes it possible to monitor the total pressure in the reactor 1.

The temperature in the reactor 1 is measured by a thermometric device 14 and can be modified by circulating a fraction of the reaction liquid in a cooling loop passing through a heat exchanger 15 supplied with a cooling fluid via a valve 30.

The stream of reaction material thus removed from the reactor, and then cooled and recycled, makes it possible to remove about 20% of the heat of the acetic acid formation reaction.

The vents leave the top part of the reactor 1 through a line 16.

The flow rate of gas purged at the top of the reactor 1 is adjusted so as to maintain a carbon monoxide partial pressure of 10 bar in the gaseous canopy of the reactor.

The vents are then introduced into a gas-liquid separator 17, which returns the liquid part to the reactor 1 and sends the gaseous part to a washing column 19, in which the gas is washed with acetic acid or methanol before being passed through a flare stack 18 and discharged into the atmosphere.

In the installation shown in FIG. 1, provision has also been made for the intercalation, in the vent evacuation circuit, prior to discharge into the atmosphere, of a flow meter 20, an analyzer 21 for analyzing the gases emitted, and a calculating module 21' connected to the flow meter 20, the analyzer 21 and the flow meter 9. The analyzer 21 can be any device for continuous or sequential measurement of the content, particularly the hydrogen and/or $CO_2$ content, of the purge gases.

This analysis, coupled with measurement of the total flow rate of the plant's vents, makes it possible to determine the flow rates of hydrogen and carbon dioxide generated by the secondary reactions in the carbonylation reactor 1.

Calculation, in the module 21', of the ratio of these partial flow rates to the total flow rate of carbon monoxide entering the reactor 1 thus gives access to the selectivities.

It is also possible, by means of appropriate analyses, to check the content of different elements in the reaction medium, particularly the water content and the methyl acetate content.

Provision can also be made for monitoring the liquid level in the reactor. This can be effected by any means conventionally used for monitoring the level of a liquid in a reactor, particularly via a differential pressure measurement in a reference leg system in the reactor, shown at 37.

A fraction of the liquid constituting the reaction medium is transferred continuously via a line 31 from the reactor 1 into the flash device 2, in which the pressure is maintained at a value below that prevailing in the reactor 1 so as to produce a partial vaporization of the reaction liquid. The stream F6 of liquid introduced into the flash device 2 is measured by means of a flow meter 22a. The fraction not vaporized in the flash zone 2 returns to the reactor 1 via a line 32 and its flow rate F2 can be measured by means of a flow meter 22b.

The fraction vaporized in the flash device 2 is sent to the first distillation column 3 via a line 33. The liquid collected at the bottom of this first distillation column is returned to the flash zone, as shown by the reference 34, whereas part of the aqueous liquid phase at the top of this first column 3 is returned to the reactor 1 through a separator 23 for decantation of the two liquid phases obtained with a flow rate F3, which can be measured by means of a flow meter 24, the remainder of the aqueous fraction being returned to the top of the first distillation column 3. Furthermore, the organic liquid phase coming from the top of the distillation column 3 is also recycled into the reactor with a flow rate F4, which can be measured by means of a flow meter 25. The fraction remaining in the column 3 after removal of the top and bottom fractions is sent to a second distillation column 4 via a line 35.

Part of the liquid condensed at the top of this second column 4 is recycled with a flow rate F5 into the reactor 1 via a line 36. The flow rate of this fraction can be measured by means of a flow meter 26. The remainder of the top fraction returns to the column 4, as shown by the reference 37.

The fraction collected at the bottom of the second distillation column 4, consisting essentially of acetic acid, undergoes a final purification step in the column 5, where the acetic acid is separated from the heavy by-products collected at the bottom of the column and from the lighter products collected at the top of the column and partially recycled into the column 4.

During the operation of the installation, it happens that the carbon monoxide feed rate undergoes fluctuations associated with the production equipment located upstream.

The methanol flow rate is adjusted to the carbon monoxide flow rate in a quasi-stoichiometric manner.

The $CO_2$ selectivity is adjusted to a value less than or equal to 0.01:

by adjusting the rhodium concentration in the reaction medium to give a sufficient catalytic activity;

by adjusting the concentration of iodine-containing promoter, i.e. methyl iodide, there being a buffer stock of methyl iodide in the decanter at the top of the first distillation column; increasing or decreasing this buffer volume makes it possible to adjust the methyl iodide content in the reactor and hence the activity of the catalyst system;

by adjusting the reactor temperature within a given range: 175° C. to 190° C.

To get away from the transitory states which generate uncontrolled periods of operation, a stable regime is sought which will make it possible to maintain the concentrations of the various constituents at fixed values in the reactor and properly to monitor the return streams entering the reactor; to achieve this, the aim is therefore to maintain the reactor temperature so as to maximize the acetic acid production according to the flow rate of carbon monoxide entering the reactor.

The flow rate of reaction liquid entering the flash zone is then adjusted so to remove the remaining heat of reaction.

When controlling the installations in conventional manner, the loss of carbon monoxide, or excess CO, was 2% by volume, based on the total CO feed.

It was then sought to reduce the largest fluctuations in carbon monoxide flow rate by stepwise variation of the reactor temperature so as to maximize the acetic acid production and avoid transitory regimes at the origin of uncontrolled periods of operation.

The objective was then to fix the temperature value in order to stabilize the concentrations of the various species in the reactor, as well as the streams.

Example 2

Figure 2:
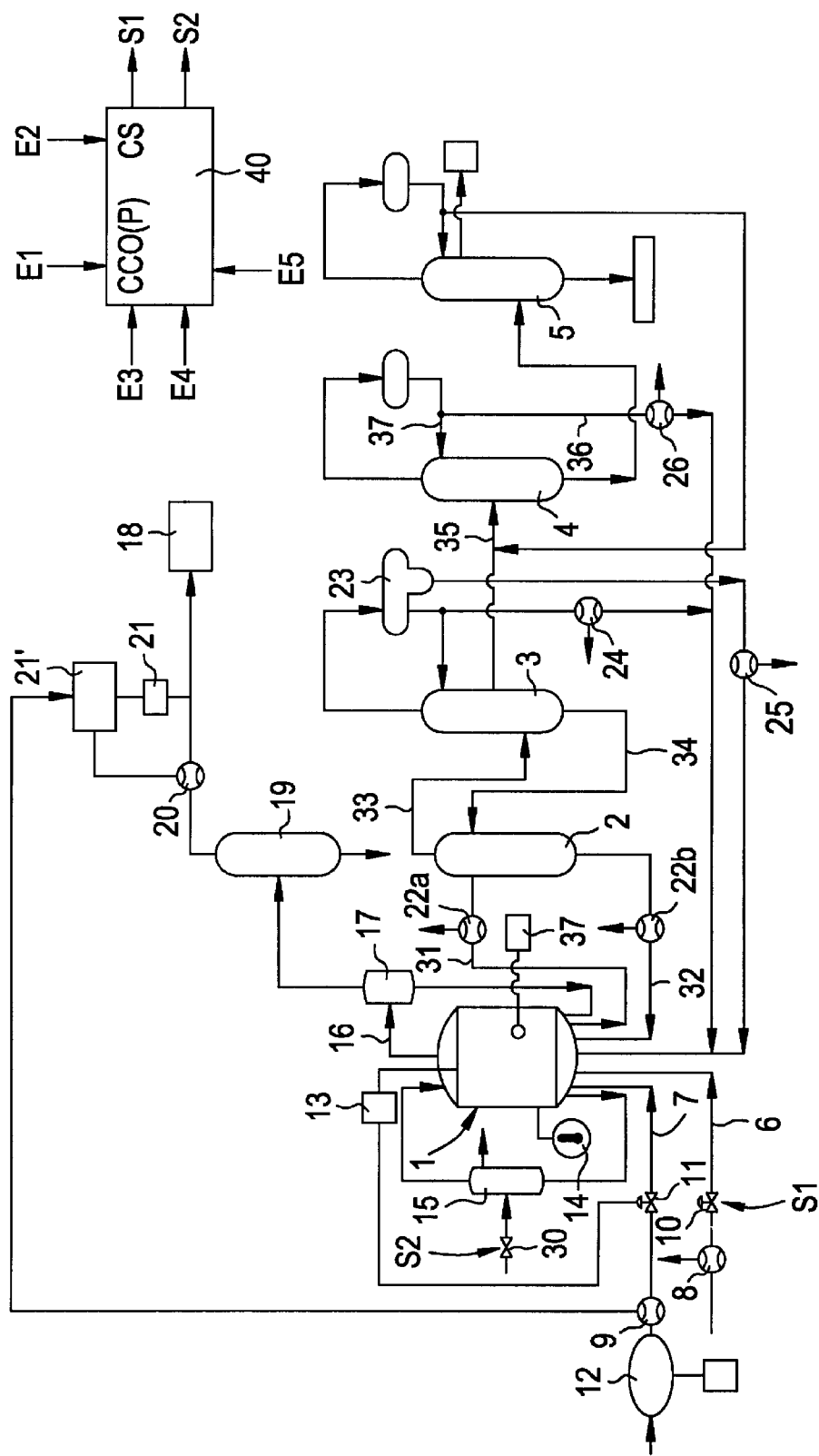
FIG. 2 shows the diagram of an improved installation according to the invention. This Figure is given with reference to Example 2.

This Example illustrates how the process according to the invention is carried out in order to manufacture acetic acid under the operating conditions of Example 1 in an installation shown diagrammatically in FIG. 2.

The installation shown in FIG. 2 represents an improvement to the installation shown in FIG. 1, incorporating a multivariable predictive controller 40.

Be The controller 40 is programmed to regulate objective variables around set values by acting on action variables.

In this Example 2 the objective variables which it is sought to regulate are the carbon monoxide feed rate in the reactor 1 and the $CO_2$ selectivity. The action variables are the temperature inside the reactor 1 and the methanol feed rate in this reactor.

More particularly, the controller 40 receives:

at a first input E1, the carbon monoxide feed rate in the reactor 1 as measured by the flow meter 9;

at a second inlet E2, the $CO_2$ selectivity of the reaction as calculated by the calculating module 21' as a function of the analysis results obtained by the analyzer 21, the flow rate value measured by the flow meter 20 and the CO feed rate measurement given by the flow meter 9;

at a third input E3, the methanol feed rate in the reactor 1 as measured by the flow meter 8; and at a fourth input E4, the temperature inside the reactor 1 as measured by the thermometric device 14.

For reasons of clarity, the connections between the controller and the rest of the installation have not been shown in FIG. 2.

At a given moment, the controller 40 compares the objective variables (CO flow rate and selectivity) with set values CCO and CS and outputs control signals S1 and S2 which depend on:

the difference between each of the objective variables and its set value, the methanol feed rate measurement and the temperature measurement in the reactor 1, and the relationships between the action variables and the objective variables recorded in the controller when it was programmed.

The control signals S1 and S2 are used respectively to control the valve 10 for controlling the methanol feed rate in the reactor 1 and the valve 30 for controlling the cooling fluid feed rate in the heat exchanger 15 so that the carbon monoxide flow rate and the $CO_2$ selectivity approach their set values CCO and CS.

The set value CS around which the $CO_2$ selectivity is regulated is a predetermined fixed value preferably chosen to be less than or equal to 0.01.

The set value CCO around which the carbon monoxide flow rate is regulated varies as a function of the availability of carbon monoxide in the CO reservoir 12 upstream of the reactor 1. This availability is ascertained directly by measuring the pressure P in the buffer reservoir 12 by means of a pressure controller 38. The set value CCO is calculated by the controller 40 as a function of the pressure P, which is applied to a fifth input E5 of the controller, as shown in FIG. 2.

Bringing the temperature in the reactor 1 and the methanol feed rate in said reactor under the control of the carbon monoxide flow rate and the $CO_2$ selectivity, as described above, makes it possible on the one hand to reduce the excess carbon monoxide stream, i.e. the carbon monoxide losses, and on the other hand to maintain the $CO_2$ selectivity at a predetermined value and hence to maintain the methyl acetate concentration.

There now follows a description of how the process according to the invention is carried out in this Example 2.

The controller chosen as the controller 40 is the IDCOM-HIECON device, which is a multivariable blackbox model based predictive controller designed for continuous manufacturing processes. It was developed by ADERSA.

This controller was preprogrammed as follows:

A mathematical control model was selected from a library of known given models of the controller with the aid of prerecorded tests.

An experimental phase was then carried out in the form of process stress tests, without control, which took place over two days.

The signals collected on the industrial site at 5-second intervals were filtered through an anti-aliasing filter and were saved at 2-minute intervals for identification.

Firstly, after a two-hour stabilization period, the temperature of the reactor was increased rapidly by an increment of 0.5° C.; once temperature incrementation was finished, the change in the parameters was followed until a plateau was reached in terms of the $CO_2$ selectivity and the carbon monoxide feed rate (a duration of about two hours).

The reactor temperature was again increased rapidly by 0.5° C. and the parameters were followed (a duration of about two hours).

The temperature was then lowered twice by 0.5° C. with the parameters being followed.

The same operations were performed the next day by lowering the methanol flow rate twice by 0.5 T/h and then increasing it twice by an increment of 0.5 T/h.

Following the parameters consisted more particularly in continuously measuring the values of the action variables (temperature in the reactor 1 and flow rate of methanol entering said reactor) and the values of the objective variables (flow rate of carbon monoxide entering the reactor 1 and $CO_2$ selectivity).

Final adjustments were made to the controller using the HIECON software supplied by the manufacturer. The measured values of the different parameters were supplied to the controller. The software then optimized the gain and lag parameters to be applied to the output signals S1 and S2.

After the controller had been programmed, it was put into operation as shown in FIG. 2 and the process was carried out under the same conditions as in Example 1 described above.

It was then found, surprisingly and unexpectedly, that by virtue of the controller 40 it was possible to maintain the variation in $CO_2$ selectivity within narrow limits while at the same time varying the temperature of the reaction mixture and the methanol feed rate so as to be able to maximize the carbon monoxide consumption and hence maximize the acetic acid production.

Installation of the controller made it possible to reduce the excess CO flow rate to 0.5%, based on the total flow rate of CO feed, thereby affording a 1.5% increase in acetic acid productivity over a representative 5-month period. This corresponded to an increase in acetic acid production of more than 2000 tonnes over this 5-month period, based on the same quantity of available CO.

The use according to the invention of a multivariable predictive controller in a process such as that described in Comparative Example 1 made it possible to satisfy the various constraints, some of which are conflicting. In fact, in the prior art, it was sought to keep the temperature as constant as possible in order to stabilize the other parameters, but the carbon monoxide flow rate exhibited fluctuations.

Example 3

This Example again refers to the industrial installation and the device employed in Example 2.

However, the controller 40 is also used in this case to bring the recycle streams entering the reactor 1 under the control of the liquid level in said reactor.

The main liquid streams entering the reactor 1 are:

the methanol feed rate—F1 the recycle streams passing from zones II and III to the reactor, namely:

the recycling of the liquid fraction from the flash zone together with the liquid from the bottom of the first distillation column—F2 the recycling of part of the aqueous liquid phase from the top of the first distillation column—F3 the recycling of the organic liquid phase from the top of the first distillation column—F4 the recycling of part of the condensed liquid from the top of the second distillation column—F5

The main liquid stream leaving the reactor consists of the flow passing from the reactor to the flash zone—F6.

With the stream F1 already incorporated in the multivariable controller, it suffices to add the streams F2, F3, F4, F5 and F6, measured respectively by the flow meters 22b, 24, 25, 26 and 22a, as the action variables, and the liquid level in the reactor 1, measured by the device 37, as the objective variable.

There are therefore three objective variables:

the quantity of CO consumed the $CO_2$ selectivity the liquid level in the reactor and seven action variables:
the methanol flow rate F1
the reactor temperature
the flow rates F2, F3, F4, F5 and F6

However, the new control objective, relating to the liquid level in the reactor, can be achieved in different ways.

For example, it is possible to choose only the flow rates F2, F4, F5 and F6 as the flow rate action variables (i.e. to omit the flow rate F3) and to compensate this by adding to the controller a fixed relationship between the flow rates F4 and F3 as a secondary objective.

To reduce the number of action variables further, it is also possible to set complementary secondary objectives such as maintenance of the value of the ratio F2/F1 and maintenance of the value of the ratio F6/F1.

It is thus possible automatically to control the main liquid streams of the acetic acid production installation while at the same time maximizing the acetic acid production by making the best use of the available carbon monoxide.

In this Example 3, the tests prior to the programming of the controller 40 were performed as follows:

The relationships between the different variables were constructed by creating several variations in the action variable for each action variable/objective variable pairing (the pairing in this case being particularly between on the one hand the different flow rates and on the other hand the liquid level in the reactor) and observing the influence of these variations on the objective variable while keeping the other parameters constant.

The signals collected on the industrial site at 5-second intervals were filtered through an anti-aliasing filter and saved at 2-minute intervals for identification.

The tests took place over several days with incremental modification of only one of the flow rates (F1, F2, F4, F5, F6) over a one-day period, the flow rate F3 having been given a set value in direct proportion to the methanol feed rate.

The increments of each parameter were chosen according to the amplitude of the perturbations generated over the plant as a whole.

Thus the positive or negative increments were 0.2 T/h for F1, 2 T/h for F2, 0.5 T/h for F4 and F5 and 15 T/h for F6.

The HIECON software was then used to optimize the control parameters.

The controller was then put into operation in the installation.

Example 4

In this Example the carbonylation of methanol is carried out in a continuous pilot installation which reproduces the operating principle of the industrial plant with a stirred reactor, a flash zone and the recycling of the liquid phase (containing the catalyst species) from the flash separator into the reactor.

Distillation is not performed and the recycling of the zone III streams is simulated by the introduction of so-called fresh reactants (a mixture of acetic acid, methyl acetate, methyl iodide and water); the catalyst lost by entrainment in the vapor phase of the flash separator is periodically reintroduced into the reactor in the form of fresh catalyst.

The composition of the reaction medium is as follows:
Water: 7%
Methyl iodide: 10%
Methyl acetate: 15%
Iridium: 1250 ppm
Acetic acid: to 100%

The total pressure is 35 bar and the reactor temperature is 190° C.

The carbon monoxide partial pressure is 23 bar.

The carbonylation rate is 15.5 mol/(h.l) under these conditions.

The $CO_2$ selectivity is 0.01, the hydrogen selectivity has a value of 0.001 and the methane selectivity has a value of 0.009.

In this Example of a pilot installation, the main objective is not to optimize the utilization of the available carbon monoxide but to achieve reaction conditions and operating conditions which are sufficiently stable to validate and optimize the activity of the catalyst medium.

The parameters for controlling the rhodium catalysis of Example 2 can no longer be used: in fact, the variation in $CO_2$ selectivity is relatively small over the chosen operating range, so it does not allow monitoring of the methyl acetate content.

Furthermore, the chemistry at low water contents is very sensitive to the water content, which is a direct parameter of the kinetics of the acetic acid production reaction.

This therefore makes it necessary to follow this water content continuously in the reactor:
either by direct measurement
or by calculation, allowing for the water concentrations in the various recycle streams entering the reactor.

A near infrared spectrometric analyzer afforded in situ determinations of the contents of water, methyl acetate, methyl iodide and acetic acid in the reaction medium with response times of less than one minute.

The analyzer employed was the 5000 model from NIR-Systems.

It was calibrated as follows:
the analyzer is switched to automatic acquisition (saving of the spectra)
a sample is taken at each different operating point
the sample is determined by gas chromatography (reference method)
the spectrum corresponding to the sampling time is selected
the spectra-concentrations database is enriched A mathematical model is then created to determine, in real time, the concentrations of the three main constituents selected: water, methyl acetate and methyl iodide.

The prediction errors were then determined:
water: 0.2% for a range of 0.5% to 21%
methyl acetate: 0.4% for a range of 0.5% to 24%
methyl iodide: 0.7% for a range of 2% to 14%

The controller is used in this Example 4 to regulate two objective variables:
the flow rate of CO consumed
the water content of the reaction medium
by acting on two action variables:
the temperature of the reaction medium in the carbonylation reactor
the flow rate of methanol feed The installation of this controller made it possible automatically to maintain the following parameters at predetermined values without human intervention:
the flow rate of CO consumed
the water content
over whole cycles of several hours for testing catalyst systems with a low water content.

The tests prior to programming of the controller consisted in general terms in creating several variations of the action variable for each action variable/objective variable pairing and observing the influence of these variations on the objective variable while keeping the other parameters constant.

The signals collected on the industrial site at 5-second intervals were filtered through an anti-aliasing filter and were saved at 2-minute intervals for identification.

The HIECON software then enabled the controller to be adapted to the problem.

What is claimed is:

1. A continuous preparative process, including monitoring production, for a product selected from the group consisting of acetic acid, methyl acetate and mixtures thereof, by carbonylation, in an industrial installation, of methanol or a carbonylatable derivative of methanol with carbon monoxide in a liquid phase in the presence of water and a homogeneous catalyst system, said preparative process comprising the steps of:

in a reaction zone I comprising a reactor, carrying out said carbonylation in the liquid phase at a temperature of 150 to 250° C., under a pressure of $5 \cdot 10^5$ to $200 \cdot 10^5$ Pa and with venting of part of a gaseous canopy above a liquid phase level in said reactor;

in a vaporization or flash zone II, partially vaporizing a liquid originating from the zone I at a pressure below that of zone I, to form a liquid fraction which is recycled into the reactor and a vaporized fraction; and in a purification zone III, distilling the vaporized fraction originating from said flash zone II on at least one distillation column, and recovering at an outlet of said at least one distillation column said product selected from the group consisting of acetic acid, methyl acetate and mixtures thereof, other constituents of said vaporized fraction being at least partially recycled into said reactor, wherein reactor temperature and feed rate of the methanol or carbonylatable derivative in said reactor are brought under control of the carbon monoxide feed rate and of at least one of the parameters defining the composition of the reaction medium, or of the venting or of both the reaction medium and of the venting.

2. The process according to claim 1, wherein the control is effected via a multivariable predictive controller.

3. The process according to claim 1, wherein water concentration in the reaction medium is maintained at a value greater than or equal to 14% by weight.

4. The process according to claim 3, wherein the reactor temperature and the methanol feed rate are brought under the control of carbon monoxide feed rate and $H_2$ or $CO_2$ selectivity, which is maintained at a value less than or equal to 0.01, or of methyl acetate concentration, which is maintained at a value of less than 5% by weight, based on the weight of the reaction medium, or of both said feed rate and selectivity and said methyl acetate concentration.

5. The process according to claim 1, wherein water concentration in the reaction medium is maintained below 14% by weight, based on the weight of said reaction medium.

6. The process according to claim 5, wherein reactor temperature and flow rate of methanol or carbonylatable derivative entering said reactor are brought under the control of carbon monoxide feed rate and water concentration in the reaction medium, said concentration being maintained at a predetermined set value.

7. The process according to claim 1, wherein flow rate of liquid from the reactor into flash zone II and flow rates of recycled liquid from zones II and III into said reactor are also brought under the control of the liquid phase level in said reactor so that said level remains fixed at a predetermined value.

8. The process according to claim 1, wherein water concentration in the reaction medium is monitored and regulated.

9. The process according to claim 1, wherein variations in carbon monoxide feed rate are damped via a buffer reservoir placed upstream of said reactor.

10. The process according to claim 9, wherein a set value of carbon monoxide flow rate depends on pressure inside said buffer reservoir.

11. The process according to claim 1, wherein fluctuations in flow rate of carbon monoxide entering the reactor are damped by discharging at least part of an excess into the atmosphere.

12. The process according to claim 1, wherein a portion of heat produced by the process is removed or recovered.

13. The process according to claim 1, further comprising measuring concentration of at least one product selected from the group consisting of water and methyl acetate.

14. The process according to claim 13, wherein said at least one product is measured using an analyzer operating in the near infrared.

15. The process according to claim 11, wherein the catalyst system comprises at least one group VIII metal.

16. The process according to claim 15, wherein said at least one group VIII metal is selected from the group consisting of rhodium, iridium and platinum.

17. The process according to claim 15, wherein said catalyst system also comprises a co-catalyst.

18. The process according to claim 17, wherein said co-catalyst is methyl iodide.

19. The process of claim 18, further comprising measuring concentration of at least one product selected from the group consisting of water, methyl acetate and methyl iodide.

20. The process according to claim 19, wherein said at least one product is measured using an analyzer operating in the near infrared.

21. The process according to claim 1, wherein methanol is carbonylated.

22. A method for monitoring a continuous preparative process of production of a product selected from the group consisting of acetic acid, methyl acetate and mixtures thereof, by carbonylation, in an industrial installation, of methanol or a carbonylatable derivative of methanol with carbon monoxide in a liquid phase in the presence of water and a homogeneous catalyst system, said preparative process comprising the steps of:

in a reaction zone I comprising a reactor, carrying out said carbonylation in the liquid phase at a temperature of 150 to 250° C., under a pressure of $5 \cdot 10^5$ to $200 \cdot 10^5$ Pa and with venting of part of a gaseous canopy above a liquid phase level in said reactor;

in a vaporization or flash zone II, partially vaporizing a liquid originating from the zone I at a pressure below that of zone I, to form a liquid fraction which is recycled into the reactor and a vaporized fraction; and in a purification zone III, distilling the vaporized fraction originating from said flash zone II on at least one distillation column, and recovering at an outlet of said at least one distillation column said product selected from the group consisting of acetic acid, methyl acetate and mixtures thereof, other constituents of said vaporized fraction being at least partially recycled into said reactor, wherein said monitoring method comprises bringing reactor temperature and feed rate of the methanol or carbonylatable derivative in said reactor under control of the carbon monoxide feed rate and of at least one of the parameters defining the composition of the reaction medium or of the venting or of both the reaction medium and the venting.

23. The method according to claim 22, wherein the control is effected via a multivariable predictive controller.

24. The method according to claim 22, wherein water concentration in the reaction medium is maintained at a value greater than or equal to 14% by weight.

25. The method according to claim 24, wherein the reactor temperature and the methanol feed rate are brought under the control of carbon monoxide feed rate and $H_2$ or $CO_2$ selectivity, which is maintained at a value less than or equal to 0.01, or of methyl acetate concentration, which is maintained at a value of less than 5% by weight, based on the weight of the reaction medium, or of both said carbon monoxide feed rate and said $H_2$ or $CO_2$ selectivity and said methyl acetate concentration.

26. The method according to claim 22, wherein water concentration in the reaction medium is maintained below 14% by weight, based on the weight of said reaction medium.

27. The method according to claim 26, wherein reactor temperature and flow rate of methanol or carbonylatable derivative entering said reactor are brought under the control of carbon monoxide feed rate and water concentration in the reaction medium, said water concentration being maintained at a predetermined set value.

28. The method according to claim 22, wherein flow rate of liquid from the reactor into flash zone II and flow rates of recycled liquid from zones II and III into said reactor are also brought under the control of the liquid phase level in said reactor so that said level remains fixed at a predetermined value.

29. The method according to claim 22, wherein water concentration in the reaction medium is monitored and regulated.

30. The method according to claim 22, further comprising measuring concentration of at least one product selected from the group consisting of water and methyl acetate.

31. The method according to claim 30, wherein said at least one product is measured using an analyzer operating in the near infrared.

32. The method according to claim 22, wherein the catalyst system comprises at least one group VIII metal as a catalyst and methyl iodide as a co-catalyst.

33. The method of claim 32, further comprising measuring concentration of at least one product selected from the group consisting of water, methyl acetate and methyl iodide.

34. The method according to claims 33, wherein said at least one product is measured using an analyzer operating in the near infrared.

* * * * *